United States Patent

Lundvik

[11] Patent Number: 5,797,740
[45] Date of Patent: Aug. 25, 1998

[54] DENTAL INSTRUMENT

[75] Inventor: Kjell Per Lundvik, Neuenegg, Switzerland

[73] Assignee: Develodent GmbH, Neuenegg, Switzerland

[21] Appl. No.: 835,816

[22] Filed: Apr. 16, 1997

[30] Foreign Application Priority Data

Apr. 17, 1996 [EP] European Pat. Off. ............ 96810242

[51] Int. Cl.$^6$ .................................. A61C 1/00; A61C 3/00
[52] U.S. Cl. ........................ 433/29; 433/141; 433/149
[58] Field of Search ........................ 433/29, 141, 149, 433/215, 229

[56] References Cited

U.S. PATENT DOCUMENTS

| | | | |
|---|---|---|---|
| 4,666,405 | 5/1987 | Ericson | 433/229 |
| 4,666,406 | 5/1987 | Kanca, III | 433/229 |
| 4,696,646 | 9/1987 | Waitland | 433/149 |
| 4,726,770 | 2/1988 | Kurer | 433/229 |
| 4,888,489 | 12/1989 | Bryan | 433/29 X |
| 5,017,140 | 5/1991 | Ascher | 433/229 X |
| 5,030,093 | 7/1991 | Mitnick | |
| 5,098,292 | 3/1992 | Lazarof | 433/141 |
| 5,271,734 | 12/1993 | Takeuchi | 453/29 X |

FOREIGN PATENT DOCUMENTS

| | | |
|---|---|---|
| 4133109 | 2/1993 | Germany . |
| 9413725 | 11/1994 | Germany . |

*Primary Examiner*—Nicholas D. Lucchesi
*Attorney, Agent, or Firm*—Foley & Lardner

[57] ABSTRACT

The instrument for the handling of dental fillings is characterized in that it is provided at one of its ends or at both ends with a head comprising a stuffing part which is made of a light transmitting or light conducting material and which can be connected to a light source. Preferably, the stuffing part is removably fastened to the head. Such an instrument allows a good exposure with light and thus provides good contact points of tooth fillings to be hardened as well as a good handling of the fillings.

7 Claims, 2 Drawing Sheets

DENTAL INSTRUMENT

BACKGROUND OF THE INVENTION

The present invention is related to a dental instrument for the handling of tooth fillings. A plurality of dental instruments have already become known, and a variety of different dental instruments and accessories have been put on the market, especially recently, which are designed for placing fillings of synthetic material to the desired site or to keep them in place, and to irradiate them with light for allowing their hardening.

The German Publication No. 4,133,109 discloses a dental instrument having an exchangeable lightconducting stuffing part, whereby the light source is freely applied onto one spherical surface of the stuffing part. It is relatively difficult to use this instrument since two hands are needed for using the instrument and for applying the light source.

German Utility Model No. 9,413,725 discloses an instrument having not any more the above mentioned drawback in needing two hands in that the light source is connected to the end of the handle of the instrument away from the end having the stuffing part. The disclosed coupling of the light from the source to the stuffing part and onto the tooth to be treated is complicated and incurs severe losses of light.

U.S. Pat. No. 5,098,292 discloses a dental instrument where the light source is connected to the one end of the handle not having the stuffing part, with relatively complicated coupling means.

The U.S. Pat. No. 5,030,093 discloses a similar dental instrument as the above mentioned one, where the light coupling parts are screwed together resulting also in losses of light.

SUMMARY OF THE INVENTION

Starting from this prior art, it is an object of the present invention to provide a dental instrument for the handling of tooth fillings which is relatively simple and therefore efficient without much loss of light and which allows above all a better exposure of dental fillings to be hardened. Such a dental instrument is defined in the independent claim, wherein at least one end of the instrument is provided with a head having a stuffing part made of a light transparent or light conducting material, the head being adapted to receive an attachable light source at its end which is remote from the stuffing part.

Further features and advantageous embodiments of the invention are defined in the dependent claims and will become evident to the one skilled in the art from the following description of a preferred embodiment of the dental instrument with the aid of the drawing.

DETAILED DESCRIPTION OF THE INVENTION

Figure 1:
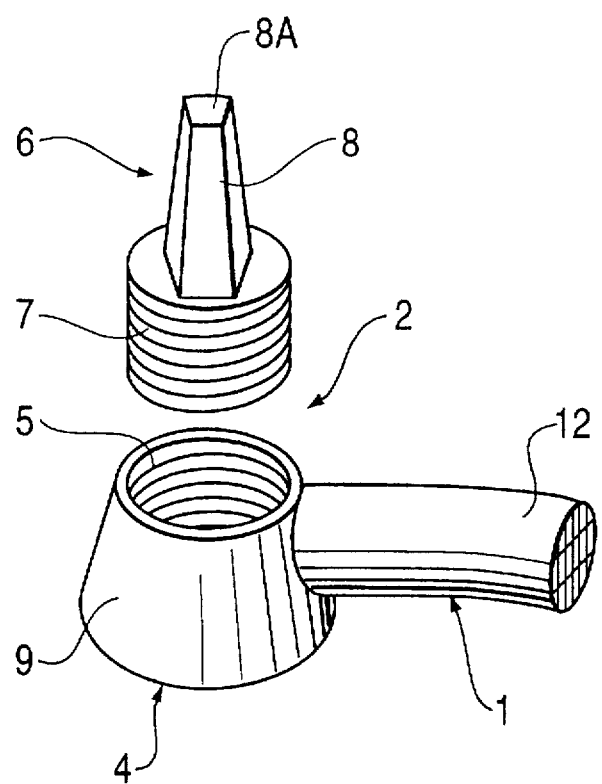
FIG. 1 is a perspective view of parts of a dental instrument according to the invention.
Figure 2:
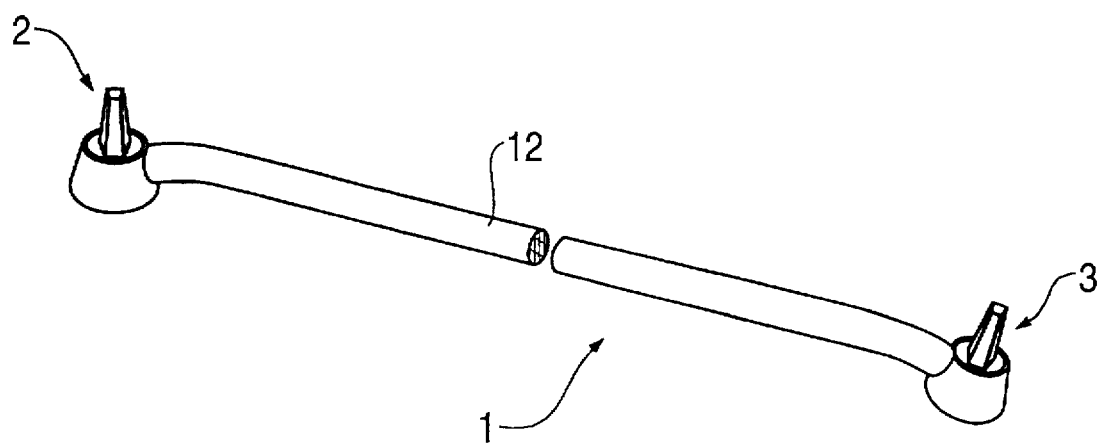
FIG. 2 shows a complete overview of the dental instrument.

FIG. 2 shows the dental instrument 1 having two end portions 2 and 3. The middle portion 12 of the instrument is shaped as already known. The end portion 2 comprises a head 4 which is provided with a through bore having an inside thread 5. A stuffing part 6 having a thread portion 7 fits into the inside thread 5, and this thread portion bears a stuffing end 8 having a trapezoidal section which is in principle already known. The upper end surface 8A of the stuffing end 8 is parallel to the entry plane of the head 4.

It is essential for the invention that this stuffing part consists of a light transparent or light conducting material, for example of a transparent synthetic material. Preferably, the outside 9 of the head is tapered against the stuffing part. Furthermore, it is shown in FIG. 2 that both end portions of the stuffing parts, respectively, are arranged in a mirror image to each other.

Figure 3:
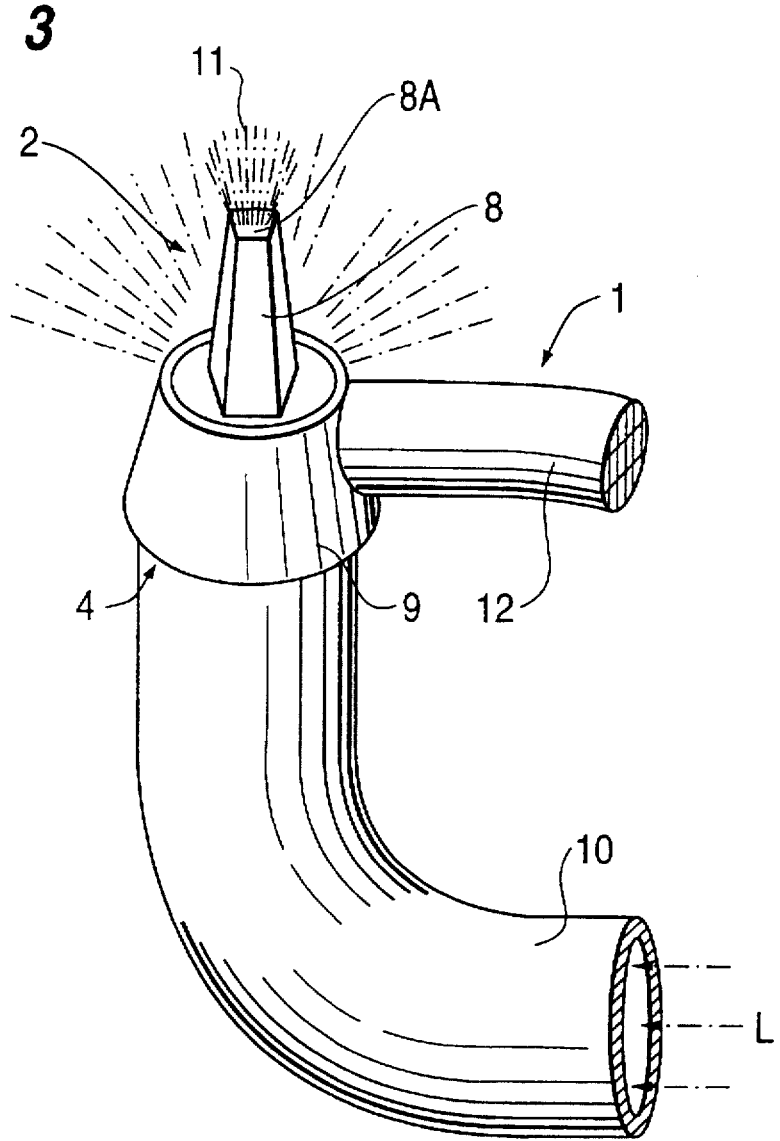
FIG. 3 shows a portion of the dental instrument provided with a light source attached thereto.

FIG. 3 shows the end portion 2 of the instrument 1 where a light conductor 10, already known per se, is attached to the parallel end which is remote from the stuffing part. Since the end of the light source is close to the entry surface of the stuffing part low losses of the light occur, whereby both surfaces can be adapted in geometry and coatings to have as low losses as possible.

The halo like crown 11 represents how the light emerges from the stuffing end 8, the greatest amount thereof coming out of the surface 8A. The amount of light emerging from the stuffing end is substantially higher and better distributed than that which comes out of a light conducting wedge, and the dental filling is thus better hardened or cured.

In order to keep the loss of light as low as possible, it may be appropriate to provide the interior of the stuffing part with light deflecting elements, i.e. such having metal coated faces, in order to obtain better directed light emerging from the stuffing end 8. It may also be appropriate to metal coat one or more outer surfaces of the stuffing end in order to concentrate the emerging light to a predetermined direction.

What I claim is:

1. A dental instrument for use in filling cavities with a light activated filling component, comprising:
    a grip having first and second ends, wherein at least one of said first and second ends of said grip bears a through bore disposed orthogonally to the length direction of said grip; and
    a plurality of light transparent stuffing parts which are removably fastenable within said through bore, said stuffing parts each including a stuffing end disposed at a first free end, and a second free end remote of said stuffing end which is adapted to receive an attachable light source.

2. The dental instrument as defined in claim 1, wherein said through bore includes an inside thread and at least one of said stuffing parts includes a thread portion fittable into said inside thread.

3. The dental instrument as defined in claim 1, wherein said stuffing end has a trapezoidal section.

4. The dental instrument as defined in claim 3, wherein said stuffing end has an upper surface disposed in parallel with said second free end of said stuffing part.

5. The dental instrument as defined in claim 1, wherein said through bore is contained within a head fixed at said grip, the outside of said head being tapered towards said stuffing end when a stuffing part is held therein.

6. The dental instrument as defined in claim 5, wherein said head further includes means for conducting the light coming from said attachable light source.

7. The dental instrument as defined in claim 1, wherein first and second stuffing parts are disposed at respective ends of said grip.

* * * * *